(12) United States Patent
Zahr

(10) Patent No.: US 8,415,470 B2
(45) Date of Patent: Apr. 9, 2013

(54) DI-ISOIMIDE COMPOSITION

(75) Inventor: George Elias Zahr, Glen Mills, PA (US)

(73) Assignee: E I du Pont de Nemours and Company, Wilmington, DE (US)

(*) Notice: Subject to any disclaimer, the term of this patent is extended or adjusted under 35 U.S.C. 154(b) by 94 days.

(21) Appl. No.: 13/168,024

(22) Filed: Jun. 24, 2011

(65) Prior Publication Data

US 2012/0330010 A1    Dec. 27, 2012

(51) Int. Cl.
*C07D 251/48* (2006.01)
*C07D 251/50* (2006.01)
*C07D 251/52* (2006.01)
*C07D 251/54* (2006.01)
*C08K 5/18* (2006.01)

(52) U.S. Cl. .......................... 544/197; 544/208; 524/100
(58) Field of Classification Search ................... 544/197, 544/208; 514/245
See application file for complete search history.

(56) References Cited

U.S. PATENT DOCUMENTS

| 3,794,641 A | 2/1974 | Gorog et al. |
| 4,546,155 A | 10/1985 | Hirose et al. |
| 6,124,381 A | 9/2000 | Miyake et al. |
| 6,576,297 B1 | 6/2003 | Cameron et al. |

FOREIGN PATENT DOCUMENTS

| GB | 1139980 A | 7/1966 |
| GB | 1192790 A | 7/1968 |
| WO | 97/31914 A | 9/1997 |

*Primary Examiner* — Venkataraman Balasubramanian

(57) ABSTRACT

The present invention deals with a novel aromatic di-isoimide chemical compound that has utility as a catalyst and as a curing agent in epoxy compositions. The di-isoimide serves effectively as a thermally activated latent catalyst in epoxy curing, thereby increasing shelf life, and avoids premature cross-linking. Novel laminated articles and printed wiring boards, including encapsulated printed wiring boards are also disclosed. The composition hereof also can be used as a flame retardant in thermoplastic and thermoset polymers.

2 Claims, 1 Drawing Sheet

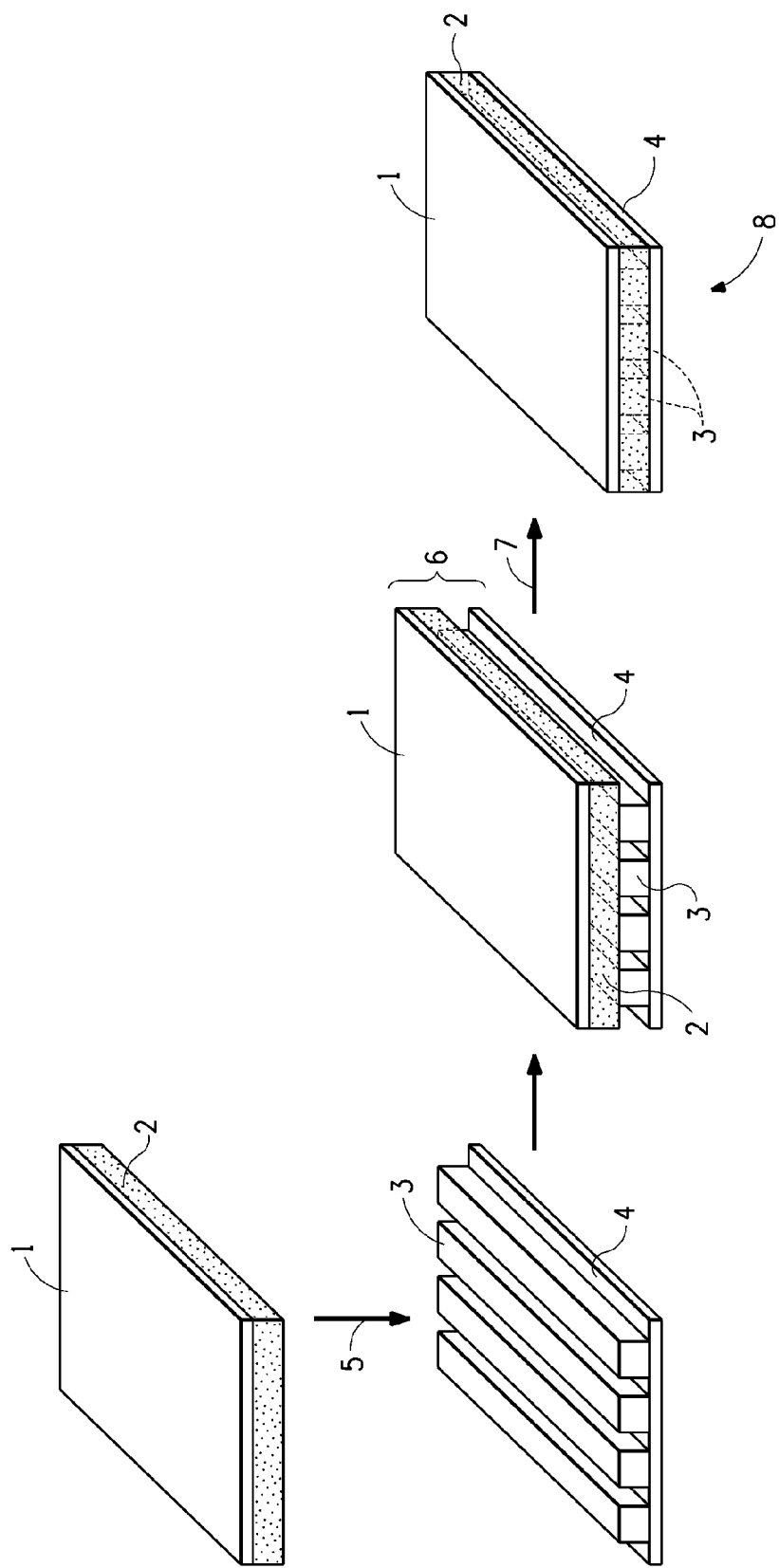

DI-ISOIMIDE COMPOSITION

RELATED PATENT APPLICATIONS

This patent application is related to U.S. patent application Ser. No. 13/168,047 entitled "Curable composition comprising a di-isoimide, method of curing, and the cured composition so formed;", U.S. patent application Ser. No. 13/168,062 entitled "Laminate comprising curable epoxy film layer comprising a di-isoimide and process for preparing same;" U.S. patent application Ser. No. 13/168,069 entitled "Printed wiring board encapsulated by adhesive laminate comprising a di-isoimide, and process for preparing same;" and, U.S. patent application Ser. No. 13/168,081 entitled "Process for Preparing Substituted and Unsubstituted Diamino triazine aromatic di-isoimides."

FIELD OF THE INVENTION

The present invention deals with a novel aromatic di-isoimide chemical compound that has utility as a catalyst and as a curing agent in epoxy compositions. It also can be used as a flame retardant in thermoplastic and thermoset polymers.

BACKGROUND OF THE INVENTION

Epoxy compositions are widely used in many applications including, among others, the electronics industry. In some applications they are blended with rubber to provide enhanced flexibility, toughness, and adhesive strength. One such application is as a flexible cover layer for flexible printed wiring boards.

While epoxies offer many desirable properties, they are known to be undesirably flammable, often requiring the addition of a flame retardant to a curable epoxy formulation in order to meet fire resistance standards. In addition, it is desirable to have a curable epoxy composition with as long a shelf life as possible. One approach to achieving long shelf-life is to prepare a so-called latent curing catalyst or cross-linking agent (curing agent). A latent catalyst or curing agent could be inactive at room temperature but thermally activated at a temperature well above room temperature. For practical reasons, it is desirable for uncured compositions to remain stable at temperatures up to 40 or 50° C. Thus a latent catalyst or curing agent activated at a temperature above 50° C. but below a temperature that will degrade the epoxy or electronic circuit elements is highly desirable in the art. A catalyst or curing agent that further obviates the need for a flame retardant additive would be so much the better for the properties of the resultant composition.

SUMMARY OF THE INVENTION

The composition of the present invention provides a curing catalyst and cross-linking agent suitable for use in a curable epoxy composition, a curable epoxy composition prepared therewith, a cured composition prepared therefrom, a film or sheet coated with the curable composition, and an encapsulated printed wiring board comprising the cured composition.

In one aspect, the present invention provides a di-isoimide composition represented by Structure I

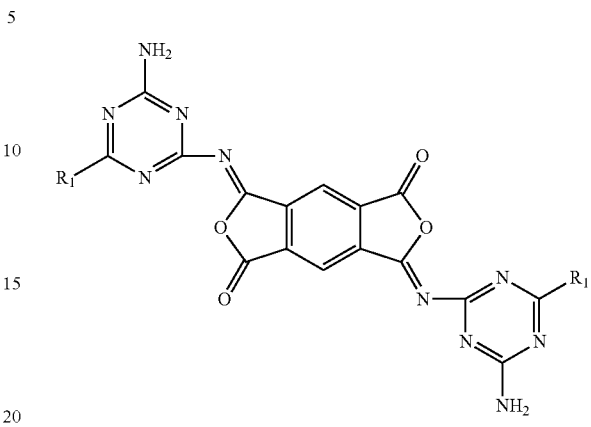

wherein $R_1$ is H, halogen, hydrocarbyl, hydrocarbyloxy, hydrocarbylthio, amido, sulfonamido, cyclic amino, acyl, morpholino, piperidino, or NR'R" where R' and R" are independently H, alkyl or aromatic, substituted or unsubstituted.

In another aspect, the invention provides a first process for preparing a di-isoimide composition represented by the Structure I, the process comprising mixing, at a temperature in the range of −10 to 160° C., in a first solvent pyromellitic dianhydride (PMDA) with a substituted or unsubstituted di-amino triazine represented by the Structure II

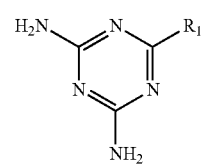

wherein $R_1$ is H, halogen, hydrocarbyl, hydrocarbyloxy, hydrocarbylthio, amido, sulfonamido, cyclic amino, acyl, morpholino, piperidino, or NR'R" where R' and R" are independently H, alkyl or aromatic, substituted or unsubstituted.

In a further aspect, the present invention provides a curable composition comprising a solvent having mixed therewithin an epoxy and a di-isoimide composition represented by Structure I

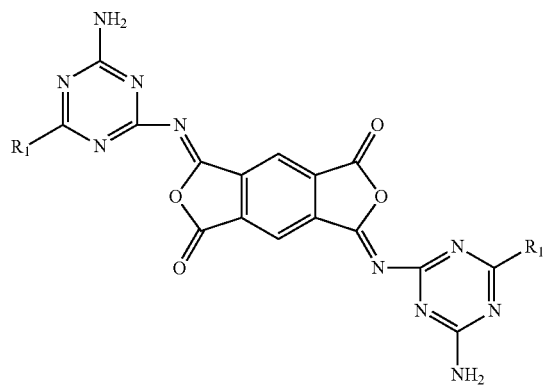

wherein $R_1$ is H, halogen, hydrocarbyl, hydrocarbyloxy, hydrocarbylthio, amido, sulfonamido, cyclic amino, acyl, morpholino, piperidino, or NR'R" where R' and R" are independently H, alkyl or aromatic, substituted or unsubstituted.

In a further aspect, the present invention provides a second process comprising heating the curable composition hereof to a temperature in the range of 100 to 250° C. for a period of time in the range of 30 seconds to 5 hours, thereby forming the corresponding cured composition.

In another aspect, the present invention is directed to a laminated article comprising a substrate and a coating deposited thereupon wherein said substrate is a polymeric sheet or film and said coating comprises a curable composition comprising a second solvent having mixed therewithin an epoxy and a di-isoimide composition represented by Structure I.

In a further aspect, the present invention is directed to a printed wiring board comprising in order a first layer of a first dielectric substrate, a second layer of one or more discrete electrically conductive pathways disposed upon said first dielectric substrate, a third layer of an adhesively bonding layer in adhesive contact with said discrete electrically conductive pathways, and a fourth layer of a second, flexible, dielectric substrate, said adhesively bonding layer comprising a curable composition comprising a second solvent having mixed therewithin an epoxy and a di-isoimide composition represented by Structure I.

In another aspect, the present invention provides a process for preparing an encapsulated printed wiring board, the process comprising adhesively contacting the coated surface of a laminated article having a surface with a coating disposed thereupon to at least a portion of the discrete conductive pathways disposed upon a dielectric substrate thereby forming a multilayer article; and, applying pressure to the printed wiring board so formed at a temperature in the range of 100 to 250° C. for a period of time in the range of 30 seconds to 5 hours, thereby forming an encapsulated printed wiring board; wherein said printed wiring board comprises in order a first layer of a first dielectric substrate, a second layer of one or more discrete electrically conductive pathways disposed upon said first dielectric substrate, a third layer of an adhesively bonding layer in adhesive contact with said discrete electrically conducting pathways, and a fourth layer of a second, flexible, dielectric substrate, said adhesively bonding layer comprising a curable composition comprising a second solvent having mixed therewithin an epoxy and a di-isoimide composition represented by Structure I.

BRIEF DESCRIPTION OF THE DRAWING

FIG. 1 is a schematic representation of the process hereof for creating the printed wiring board hereof, as described in Example 12.

DETAILED DESCRIPTION OF THE INVENTION

The term "epoxy" refers to a polymeric, generally an oligomeric, chemical comprising epoxide groups. A cross-linking agent suitable for use in the processes disclosed herein is a multifunctional molecule reactive with epoxide groups. The cross-linked reaction product thereof is the reaction product formed when the cross-linking agent reacts with the epoxide or other group in the epoxy molecule. The term "epoxy" is conventionally used to refer to the uncured resin that contains epoxide groups. With such usage, once cured, the epoxy resin is no longer actually an epoxy. However, reference to epoxy herein in the context of the cured material shall be understood to refer to the cured material. The term "cured epoxy" shall be understood to mean the reaction product of an epoxy as defined herein and a curing agent as defined herein.

The term "cured" refers to an epoxy composition that has undergone substantial cross-linking, the word "substantial" indicating an amount of cross-linking of 75% to 100% of the available cure sites in the epoxy. Preferably more than 90% of the available cure sites are cross-linked in a "fully cured" epoxy composition. The term "uncured" refers to an epoxy composition when it has undergone little cross-linking. The terms "cured" and "uncured" shall be understood to be functional terms. An uncured epoxy composition is characterized by solubility in organic solvents and the ability to undergo plastic flow under ambient conditions. A cured epoxy composition suitable for the practice of the invention is characterized by insolubility in organic solvents and the absence of plastic flow under ambient conditions. It is well-known in the art that some of the available cure sites in an uncured epoxy composition could be cross-linked and some of the available cure sites in a cured epoxy composition could remain uncross-linked. In neither case, however, are the distinguishing properties of the respective compositions significantly affected.

The art also distinguishes a partially cured epoxy composition known as a "B-stage" material. The B-stage material may contain up to 10% by weight of solvent, and exhibits properties intermediate between the substantially cured and the uncured state.

For the purposes of the present invention the term "curable composition" shall refer to a composition that comprises all the elements necessary for producing a "cured" composition, but that has not yet undergone the "curing process" and is therefore not yet cured. The curable composition is readily deformable and processable, the cured composition is not. The terms "curable" and "cured" are similar in meaning, respectively, to the terms "crosslinkable" and "crosslinked."

While the invention is not limited thereto, it is believed that the cure reaction of an epoxy with the di-isoimide hereof is mostly a reaction of an amine group of the di-isoimide to open the oxirane ring (or epoxy group, as it is often referred to) resulting in a nitrogen carbon bond, and an alkyl hydroxyl group. So in the above instance, the di-isoimide serves as a cross-linking agent. When, for example, a phenolic novolac is also present, the oxirane ring opening reaction is effected primarily by the reaction of the phenol hydroxyl group of the novolac with the oxirane ring, thereby creating an oxygen-carbon bond and an alkyl hydroxyl group. When a more active cross-linking agent, such as the phenol is not present, the di-isoimide serves as both cross-linking agent and a catalyst.

The terms "film" and "sheet" refer to planar shaped articles having a large length and width relative to thickness. Films and sheets differ only in thickness. Sheets are typically defined in the art as characterized by a thickness of 250 micrometers or greater, while films are defined in the art as characterized by a thickness less than 250 micrometers. As used herein, the term "film" encompasses coatings disposed upon a surface.

The term "discrete conductive pathway" as used herein refers to an electrically conductive pathway disposed upon a dielectric substrate in the form of a film or sheet which leads from one point to another on the plane thereof, or through the plane from one side to the other.

There are several terms that are repeated throughout this invention that are described in detail only upon the first mention thereof. However, in order to avoid prolixity the descriptions of the term are not repeated when the term reappears further on in the text. It shall be understood for the purposes of the present invention that when a term is repeated in the text hereof, the description and meaning of that term is unchanged from and the same as that provided for the term upon its first mention. For example the term "di-isoimide composition represented by Structure I" shall be understood each time it appears to encompass all the possible embodiments recited with respect to Structure I upon its first appearance in the text. For another example, the term "second solvent" shall be understood to refer to the same set of solvents described for the "second solvent" at the first appearance of the term in the text.

For the purposes of this invention, the term "room temperature" is employed to refer to ambient laboratory conditions. As a term of art, "room temperature" is normally taken to mean about 23° C., encompassing temperatures ranging from about 20° C. to about 30° C.

The term "printed wiring board" (PWB) shall refer to a dielectric substrate layer having disposed thereupon a plurality of discrete conductive pathways. The substrate is a sheet or film. In one embodiment of the invention the dielectric substrate is a polyimide film. In a further embodiment, the polyimide film has a thickness of 5-75 micrometers. In one embodiment the discrete conductive pathways are copper.

PWBs suitable for the practice of the present invention can be prepared by well-known and wide-spread practices in the art. Briefly, a suitable PWB can be prepared by a process comprising laminating a copper foil to a dielectric film or sheet using a combination of an adhesive layer, often an epoxy, and the application of heat and pressure. To obtain high resolution circuit lines (≦125 micrometers in width) photoresists are applied to the copper surface. A photoresist is a light-sensitive organic material that when subject to image-wise exposure an engraved pattern results when the photoresist is developed and the surface etched. In a suitable PWB, the image is in the form of a plurality of discreet conductive pathways upon the surface of the dielectric film or sheet.

A photoresist can either be applied as a liquid and dried, or laminated in the form, for example, of polymeric film deposited on a polyester release film. When liquid coating is employed, care must be employed to ensure a uniform thickness. When exposed to light, typically ultraviolet radiation, a photoresist undergoes photopolymerization, thereby altering the solubility thereof in a "developer" chemical. Negative photoresists typically consist of a mixture of acrylate monomers, a polymeric binder, and a photoinitiator. Upon image-wise UV exposure through a patterning photomask, the exposed portion of the photoresist polymerizes and becomes insoluble to the developer. Unexposed areas remain soluble and are washed away, leaving the areas of copper representing the conductive pathways protected by the polymerized photoresist during a subsequent etching step that removes the unprotected conductive pathways. After etching, the polymerized photoresist is removed by any convenient technique including dissolution in an appropriate solvent, or surface ablation. Positive photoresists function in the opposite way with UV-exposed areas becoming soluble in the developing solvent. Both positive and negative photoresists are in widespread commercial use. One well-known positive photoresist is the so-called DNQ/novolac photoresist composition.

Any PWB prepared according to the methods of the art is suitable for use in the present invention.

In one aspect, the present invention provides a di-isoimide composition represented by Structure I

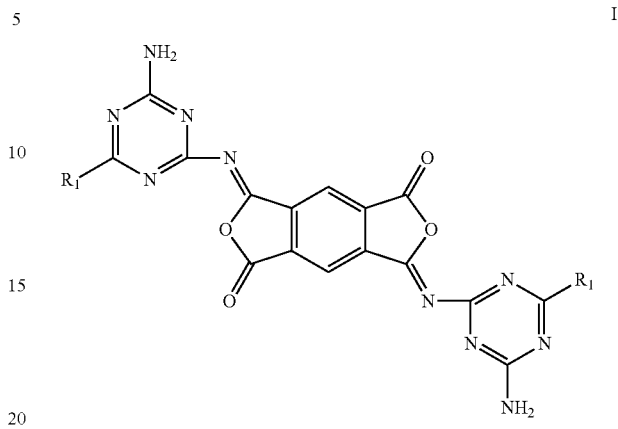

I wherein $R_1$ is H, halogen, hydrocarbyl, hydrocarbyloxy, hydrocarbylthio, amido, sulfonamido, cyclic amino, acyl, morpholino, piperidino, or NR'R" where R' and R" are independently H, alkyl or aromatic, substituted or unsubstituted. In one embodiment, $R_1$ is $NH_2$.

In another aspect, the present invention provides a first process that can be used to prepare the composition represented by the Structure I, the first process comprising mixing in a first solvent, at a temperature in the range of −10 to +160° C., PMDA with a di-amino triazine represented by the Structure II

II wherein $R_1$ is H, halogen, hydrocarbyl, hydrocarbyloxy, hydrocarbylthio, amido, sulfonamido, cyclic amino, acyl, morpholino, piperidino, or NR'R" where R' and R" are independently H, alkyl or aromatic, substituted or unsubstituted.

In one embodiment, $R_1$ is $NH_2$.

Suitable first solvents include but are not limited to polar/aprotic solvents characterized by a dipole moment in the range of 1.5 to 3.5 D. While the reaction between the aminoazine and PMDA takes place in solution, full miscibility of the reactants in the solvent is not necessary. Even limited solubility will permit the reaction to proceed, with additional reactants dissolving as they are consumed in the reaction. Suitable solvents include but are not limited to acetone, methyl ethyl ketone (MEK), methyl isobutyl ketone, ethyl propionate, ethyl-3-ethoxy propionate, cyclohexanone, and mixtures thereof. Mixtures thereof with small amounts (for example, less than 30% by weight) of non-polar solvents such as benzene are also suitable. In one embodiment, the solvent is cyclohexanone.

When the dipole moment is below 1.5 D, solubility of melamine, already low, becomes so low that the reaction can take weeks to go to completion. When the dipole moment of the solvent exceeds 3.5 D the rate of the reaction converting the di-isoimide to di-imide can proceed at an inconveniently rapid rate, causing excessive loss of the desired di-isoimide.

According to the first process of the invention, PMDA and a suitable diamino triazine, substituted or unsubstituted, as described supra, are combined in the presence of a suitable first solvent, and allowed to react. The reaction temperature can be in the range of −10 to +160° C. The yield of di-imide increases with increasing temperature, at the expense of the di-isoimide. While this invention is directed to the preparation of and the advantageous use of the di-isoimide, the presence of some di-imide mixed in with the di-isoimide does not necessarily have any particularly negative impact. In some instances, it could be advantageous to use a higher reaction temperature which results in lower selectivity but higher reaction rate.

In general, higher reaction temperature corresponds to faster reaction. Selectivity depends on temperature and the specific choices of dianhydride, triazine, and solvent. For example PMDA and melamine in cyclohexanone produce pure isoimide at 25° C., almost pure isoimide at 50° C., and produce about 80% isoimide at reflux (~155° C.). PMDA and melamine react faster in N,N-dimethyl formamide (DMF) than in cyclohexanone at the same temperature but the reaction continues on to form imide from a di-isoimide intermediate if the reaction is not stopped in time.

In one embodiment, the reaction temperature is in the range of room temperature to 100° C. In a further embodiment, the reaction temperature is in the range of room temperature to 50° C.

The first process hereof does not require a water scavenger (such as trifluoroacetic acid) in order to provide the desired di-isoimide as represented by Structure I. It is highly preferred in the first process hereof to omit any water scavenger, in order to avoid having subsequently to remove the water scavenger after reaction is complete.

It is observed in the practice of the invention that the di-isoimide hereof is more soluble than the analogous imide in relatively mild, low boiling point solvents such as cyclohexanone and MEK. Much stronger high boiling point solvents, such as dimethyl acetamide (DMAC) or n-methyl pyrrolidone (NMP), are required to dissolve the imide. This feature of the di-isoimide hereof is of considerable importance in the formulation of epoxies with practical commercial applicability. It is difficult to remove high boiling point solvents without also initiating the epoxy cure. For adhesive applications, particularly highly critical applications such as the fabrication of encapsulated PWBs as described herein, it is essential to have the solvent removed completely since the adhesive is sealed between the two surfaces it is binding together, and there is no place to which solvent can escape without causing bubbles and voids in the finished product. Bubbles and voids adversely affect the uniformity of the dielectric constant.

Maintaining a high degree of mixing during reaction is important for achieving full conversion of the reactants into the di-isoimide product. For example, melamine is of very limited solubility in the suitable solvents. PMDA is also only poorly soluble. In order to achieve high conversion within a commercially viable time frame, it is necessary to maintain good intermixing of the reactants with each other and with the solvent. While the invention is not thereby limited, it is believed that the solution equilibrium for the reactants causes small amounts of reactants to dissolve, and that the thus dissolved reactants react to form a precipitate of the di-isoimide, thereby causing additional reactants to dissolve. This process is believed to continue until the reactants are exhausted, and conversion is quantitative as indicated by the disappearance of the reactant peaks in the infra-red (IR) spectrograph of the solvent dispersion.

Suitable mixing can be achieved using mechanical stirring such as magnetic stirring. A satisfactory state of mixing is one wherein the dispersion of reactants (and product) in the solvent has a uniform appearance with no regions of stagnant solids. It is preferred to stir to maintain a uniform appearance throughout the duration of the reaction.

It is found in the practice of the invention, as herein exemplified infra in Examples 7 and 8, performing the first process hereof in the presence of a rubber compound containing carboxylic acid groups in solution causes the reaction to achieve a higher rate of conversion than the same reaction when run without the rubber.

In a further aspect, the present invention provides a curable composition comprising a second solvent having mixed therewithin an epoxy and a di-isoimide composition represented by Structure I. In one embodiment, the second solvent is the same as the first solvent.

Solvents suitable for use as the second solvent include but are not limited to acetone, MEK, cyclohexanone, pentanone, dioxolane, tetrahydrofuran, glycol ethers, propylene glycol methyl ether acetate (PMA), N-methyl pyrrolidone, N,N-dimethylacetamide, DMF, dimethyl sulfoxide, N,N-diethylacetamide, N,N-diethylformamide, N,N-dimethylmethoxyacetamide. Preferred solvents are MEK, cyclohexanone, PMA, and DMF. Mixtures of solvents are also suitable.

Referring to Structure I, in one embodiment, $R_1$ is $NH_2$.

Suitable epoxies for the curable composition hereof are epoxies comprising an average of at least two epoxide groups per polymer chain. Suitable epoxies include but are not limited to polyfunctional epoxy glycidyl ethers of polyphenol compounds, polyfunctional epoxy glycidyl ethers of novolak resins, alicyclic epoxy resins, aliphatic epoxy resins, heterocyclic epoxy resins, glycidyl ester epoxy resins, glycidylamine epoxy resins, and glycidylated halogenated phenol epoxy resins. Preferred epoxies include epoxy novolacs, biphenol epoxy, bisphenol-A epoxy and naphthalene epoxy. Preferred epoxies are oligomers having 1-5 repeat units. Most preferably the epoxy is bisphenol-A or novolac epoxy, especially a bisphenol A diglycidyl ether.

Epoxies can be derivatized in any manner described in the art. In particular they can be halogenated, especially by bromine to achieve flame retardancy, or by fluorine.

In one embodiment of the curable composition hereof $R_1$ is $NH_2$; the solvent is MEK, cyclohexanone, propylene glycol methyl ether acetate, DMF, or a mixture thereof; and, the epoxy is of the bisphenol-A type.

The di-isoimide represented by Structure I can serve both as a curing catalyst and/or as a curing agent in the curable composition hereof. The isoimide moiety reduces the flammability of the cured epoxy (vs. phenolic novolac, which does not have a comparable flame retardant effect) and thus reduces the need for flame retardants. In one embodiment, the curable composition further comprises a curing agent. Any curing agent known in the art can be used in the compositions and processes disclosed herein. Suitable curing agents include organic acid anhydrides and phenols. Monoanhydride curing agents are preferred for ease of handling.

In an alternative embodiment, the curable composition hereof does not include a separate curing agent. It is found in the practice of this embodiment of the invention that the nucleophilic character of the amine group is much reduced by the presence of the triazine ring and the isoimide linkage. It is further found that once one of the amine groups on the ring undergoes reaction, the second amine group becomes still less reactive. Therefore in formulating the curable composition in this embodiment, it is found that satisfactory results are achieved by treating each mole of the di-isoimide of Structure I as representing two equivalents from the standpoint of cross-linking the epoxy. A formulation on that basis that contains a 20% excess in equivalents of epoxy has been found to be satisfactory.

The curable composition hereof can include any and all of the numerous additives commonly incorporated into epoxy formulations in the art. This can include flame retardants, rubber or other tougheners, inorganic particles, plasticizers, surfactants and rheology modifiers.

In one embodiment, the curable composition hereof comprises a low molecular weight liquid epoxy that serves as a dispersion medium for the di-isoimide composition represented by Structure I. Low molecular weight epoxies, such as EPON™ Resin 828, are characterized by equivalent weight of 185-192 g/eq. However, such low molecular weight epoxies are less preferred than the pastier, more viscous, higher molecular weight high performance epoxies that are well-known in the art. Higher molecular weight epoxies, such as EPON™ Resin 1001F, are characterized by equivalent weight of 525-550 g/eq. While the reaction mixture formed from the higher molecular weight epoxies can be heated in order to lower viscosity, it is undesirable to apply heat for that purpose, especially in the presence of a catalyst, because of the risk of causing premature curing. In a highly preferred embodiment a high molecular weight epoxy is dissolved in a second solvent hereof—or, less preferably dispersed therein—into which a solution or dispersion of the di-isoimide composition of Structure I is then dispersed to form the curable composition hereof.

Suitable curing agents are phenol and aromatic anhydrides. The epoxy and the curing agent are mixed in quantities based on their equivalent weights. In the case of phenolic curing agents, 0.3-0.9 equivalent of phenol is preferred for each equivalent of epoxy has been found to be suitable. With anhydride curing agents, 0.4-0.6 equivalent of anhydride is preferred for one equivalent of epoxy.

Suitable phenol curing agents include biphenol, bisphenol A, bisphenol F, tetrabromobisphenol A, dihydroxydiphenyl sulfone, novolacs and other phenolic oligomers obtained by the reaction of above mentioned phenols with formaldehyde. Suitable anhydride curing agents are nadic methyl anhydride, methyl tetrahydrophthalic anhydride and aromatic anhydrides.

Aromatic anhydrides curing agents include but are not limited to aromatic tetracarboxylic acid dianhydrides such as pyromellitic dianhydride, biphenyltetracarboxylic acid dianhydride, benzophenonetetracarboxylic acid dianhydride, oxydiphthalic acid dianhydride, 4,4'-(hexafluoroisopropylidene)diphthalic acid dianhydride, naphthalene tetracarboxylic acid dianhydride, thiophene tetracarboxylic acid dianhydride, 3,4,9,10-perylene tetracarboxylic acid dianhydride, pyrazine tetracarboxylic acid dianhydride, and 3,4,7,8-anthraquinone tetracarboxylic acid dianhydride. Other suitable anhydride curing agents are oligomers or polymers obtained by the copolymerization of maleic anhydride with ethylene, isobutylene, vinyl methyl ether and styrene. Maleic anhydride grafted polybutadiene can also be used as a curing agent.

Suitable tougheners are low molecular weight elastomers or thermolastic polymers and contain functional groups for reaction with epoxy resin. Examples are polybutadienes, polyacrylics, phenoxy resin, polyphenylene ethers, polyphenylene sulfide and polyphenylene sulfone, carboxyl terminated butadiene nitril elastomers (CTBN), epoxy adducts of CTBN, amine terminated butadiene nitril elastomers (ATBN), carboxyl functionalized elastomers, polyol elastomers and amine terminated polyol elastomers. Epoxy adducts of CTBN, CTBN and carboxyl functionalized elastomer are preferred.

In one embodiment, the di-isoimide can be pre-dispersed in the solvent in which it was prepared. In an alternative embodiment, the di-isoimide may be added as particles to the epoxy solution and dispersed therein using mechanical agitation.

In a further aspect, the present invention provides a second process, a process for preparing a cured composition from the curable composition hereof by heating the curable composition to a temperature in the range of 100 to 250° C. for a period of time in the range of 30 seconds to 5 hours. For adhesive applications the solvent needs to be removed completely before curing, as described in the Examples, infra.

The viscosity of the uncured composition can be adjusted by either adding solvent to decrease the viscosity, or by evaporating solvent to increase viscosity. The uncured composition can be poured into a mold, followed by curing, to form a shaped article of any desired shape. One such process known in the art is reaction injection molding. In particular, the composition can be used in forming films or sheets, or coatings. The viscosity of the solution is adjusted as appropriate to the requirements of the particular process. Films, sheets, or coatings are prepared by any process known in the art. Suitable processes include but are not limited to solution casting, spray-coating, spin-coating, or painting. A preferred process is solution casting using a Meyer rod for draw down of the casting solution deposited onto a substrate. The substrate can be treated to improve the wetting and release characteristics of the coating. Solution cast films are generally 10 to 75 micrometers in thickness. The solution casting of a solution/dispersion hereof onto a substrate film or sheet to form a laminated article is further described in the specific embodiments hereof, infra.

In another aspect, the present invention is directed to a laminated article comprising a substrate and a coating adheringly deposited thereupon wherein said substrate is a polymeric sheet or film and said coating comprises a curable composition comprising a second solvent having mixed therewithin an epoxy and a di-isoimide composition represented by Structure I. In one embodiment, the substrate is a polyimide film. In a further embodiment said second dielectric substrate is a fully aromatic polyimide film or sheet. In a further embodiment the polyimide film has a thickness of 10-50 micrometers. In one embodiment, $R_1$ is $NH_2$. In one embodiment, the coating has a thickness of 10 to 75 micrometers.

In one embodiment, the substrate is coated on both sides thereof. In a further embodiment, the coatings on both sides are chemically identical.

In a further aspect, the present invention is directed to a printed wiring board comprising in order a first layer of a first dielectric substrate, a second layer of one or more discrete electrically conductive pathways disposed upon said first dielectric substrate, a third layer of a bonding layer in adhesive contact with said discrete electrically conducting pathways, and adheringly disposed upon a fourth layer comprising a second dielectric substrate, said bonding layer comprising a curable composition comprising a second solvent having mixed therewithin an epoxy and a di-isoimide composition represented by Structure I.

In one embodiment of the printed wiring board hereof, the first layer is a polyimide film having a thickness of 10-50 micrometers.

In one embodiment of the printed wiring board hereof, the electrically conductive pathways are copper.

In a further embodiment of the printed wiring board hereof, the copper electrically conductive pathways are characterized by a thickness of 10-50 micrometers and lines and spacing from 10-150 micrometers.

In one embodiment of the printed wiring board hereof, in said adhesively bonding layer said second solvent is MEK, cyclohexanone, PMA, DMF, or a mixture thereof.

In one embodiment of the printed wiring board hereof, in said adhesively bonding layer in said di-isoimide composition represented by Structure I, $R_1$ is $NH_2$.

In one embodiment of the printed wiring board hereof, the second dielectric substrate is a polyimide film or sheet. In a further embodiment said second dielectric substrate is a fully aromatic polyimide film or sheet. In a still further embodiment, said second dielectric substrate is a film or sheet comprising a polyimide that is the condensation product of PMDA and 4,4'-ODA. In a still further embodiment, said second dielectric substrate is a fully aromatic polyimide film having a thickness of 10-50 micrometers.

The printed wiring board hereof is conveniently formed by contacting the coating side of the laminated article hereof to the conductive pathways disposed upon the first dielectric substrate. The printed wiring board hereof has several embodiments that differ from one another in the degree of consolidation. In one embodiment the printed wiring board hereof is formed simply by disposing upon a horizontal surface a first dielectric substrate having one or more discrete conductive pathways disposed upon at least one surface thereof, where said conductive pathways are facing upward; followed by placing a coated side of the laminated article hereof in contact with the conductive pathways, thereby preparing a so-called "green" or uncured printed wiring board.

In a further embodiment, the green printed wiring board is subject to pressure thereby causing some consolidation. In a further embodiment the green printed wiring board is subject to both pressure and temperature. The temperature exposure may be sufficient to induce only a small amount of cross-linking or curing. This represents a so-called "B-stage" curing—an intermediate level of consolidation that causes the printed wiring board to have some structural integrity while retaining formability and proccessability. The B-stage can be followed by complete curing. Alternatively, complete curing can be effected in a single heating and pressurization step from the green state.

In one embodiment of the printed wiring board hereof, the first dielectric substrate bears conductive pathways on both sides, permitting the formation of the multi-layer construction described supra on both sides of the first dielectric substrate.

In another embodiment of the printed wiring board hereof, the second dielectric substrate is coated on both sides with a composition comprising a solution/dispersion of epoxy, a second solvent, and the di-isoimide composition represented by Structure I.

In still a further embodiment, the first dielectric substrate bears conductive pathways on both sides, and the second dielectric substrate bears a coating on both sides, that coating comprising a solution/dispersion of epoxy, a second solvent, and the di-isoimide composition represented by Structure I. This embodiment permits printed wiring boards hereof to be constructed with an indefinite number of repetitions of the basic structure of the multilayer article.

In a further embodiment, at least a portion of the conductive pathways disposed upon one side of the first dielectric substrate are in electrically conductive contact with at least a portion of the conductive pathways disposed upon the other side of the first dielectric substrate through so-called "vias" that serve to connect the two sides of the dielectric substrate.

In another aspect, the present invention provides a third process, a process for preparing an encapsulated printed wiring board, the process comprising adhesively contacting the coated surface of a laminated article having a surface with a coating disposed thereupon to at least a portion of the discrete conductive pathways disposed upon a dielectric substrate thereby forming a multilayer article; wherein said coating comprises a curable composition comprising a second solvent having mixed therewithin an epoxy and a di-isoimide composition represented by Structure I; and, applying pressure to the printed wiring board so formed at a temperature in the range of 100 to 250° C. for a period of time in the range of 30 seconds to 5 hours, thereby forming an encapsulated printed wiring board.

In one embodiment, the third process hereof further comprises extracting said second solvent before applying pressure to the printed wiring board. Solvent extraction can be effected conveniently by heating in an air circulating oven set at 110° C. for a period of time ranging from 2-20 minutes.

In one embodiment of the third process hereof, $R_1$ is $NH_2$.

In one embodiment of the third process hereof, the first and second dielectric substrates are both polyimide films.

In a further embodiment of the third process hereof, the polyimide films are fully aromatic polyimides.

In a still further embodiment of the third process hereof, the polyimide films are the condensation product of PMDA and ODA.

The invention is further described in the following specific embodiments though not limited thereby.

EXAMPLES

Determining Reaction Completion Point

In the following examples, infrared spectroscopy (IR) was employed to determine the end-point of the reaction. Small aliquots of the reacting medium were withdrawn by dropperfull, dried in a vacuum oven with $N_2$ purge at about 60° C. for about 60 minutes. Following conventional methodology for preparing solids for IR spectroscopic analysis, the resulting powder was then compounded with KBr followed by the application of pressure to the resulting compound, thereby forming a test pellet. IR absorption peaks at 1836 $cm^{-1}$ and 1769 $cm^{-1}$ were monitored to follow the increase in the concentration of the di-isoimide product. Similarly, IR absorption peaks at 1856 $cm^{-1}$ and 1805 $cm^{-1}$ characteristic of PMDA and 1788 $cm^{-1}$ characteristic of melamine were monitored to follow the consumption of reactants. When the PMDA and melamine peaks became undetectable, the reaction was considered to be complete.

Peaks at 1788 $cm^{-1}$ and 1732 $cm^{-1}$ characteristic of imide were also monitored to follow the synthesis of any imide by-product of the present process.

The time to reaction completion was observed to vary considerably with the reaction temperature and the particular choice of solvent.

Reaction Medium

Both melamine and PMDA are only slightly solubile in the solvents employed herein so it was necessary to maintain good mixing during reaction to ensure a high degree of conversion. Without constant vigorous mixing, the solids settled and the reaction slowed down or stopped. The amount of energy that was needed for mixing was determined by observation. When the dispersion was of uniform appearance and no stagnant solid phase was observed, mixing was deemed to be of sufficient energy. The di-isoimide product formed into platelet particles with dimensions in the hundreds of nanometers range. These platelet particles also remained suspended with mixing. By the time reaction was completed, no detectable amounts of PMDA or melamine were present in the reaction mixture—all the suspended particles were di-isoimide, or, in some instances, di-isoimide with some imide mixed in.

Printed Wiring Board

A Pyralux® AC182000R copper clad laminate sheet (Dupont Company) was etched according to a common commercial etching process to form a series of parallel copper conductive strips 35 micrometers high, 100 micrometers wide, and spaced 100 micrometers apart. This was used in Examples 9-12, and is referred to therein as "a PWB test sheet." Information on methods for preparing printed wiring boards can found in Chris A. Mack, Fundamental Principles of Optical Lithography: The Science of Microfabrication, John Wiley & Sons, (London: 2007). Hardback ISBN: 0470018933; Paperback ISBN: 0470727306.

Reagents

Except where otherwise noted, all reagents were obtained from Sigma Aldrich Chemical Company.

Example 1

6.31 grams of melamine, 5.45 grams of PMDA and 25 grams of MEK were mixed using a magnetic stirrer in a round bottom flask. The mixture was refluxed under nitrogen for two days until conversion was complete. MEK was added as needed during refluxing to keep the volume of the reaction mixture approximately constant. The thus prepared product mixture was cooled to room temperature while maintaining stirring. As confirmed by IR spectroscopy, the product mixture contained only MEK and di-isoimide. No imide was detectable. The dispersion so prepared was suitable for immediate use in formulating a curable epoxy composition.

Example 2

6.31 grams of melamine, 5.45 grams of PMDA and 35 grams of ethyl 3-ethoxypropionate were mixed in a round bottom flask. The mixture was refluxed under nitrogen for two days until conversion was complete. The mixture was cooled to room temperature. A small sample from the mixture was washed with MEK. As confirmed by IR spectroscopy, the product mixture contained MEK, di-isoimide, and a small amount of imide indicated by a small IR peak at 1734 $cm^{-1}$. The dispersion so prepared was suitable for immediate use in formulating a curable epoxy composition.

Example 3

69.69 grams of melamine (0.534 moles), 60.26 grams of PMDA (0.267 moles) and 360 grams cyclohexanone are added into a reaction vessel, and stirred at room temperature for 6 days until conversion was complete. A sample from the reaction mixture was dried in vacuum oven. IR spectra of the final solid product showed the disappearance of the PMDA peaks at 1856 & 1805 $cm^{-1}$ and melamine peak at 1558 $cm^{-1}$ and the appearance of the isoimide peaks at 1836 & 1769 $cm^{-1}$.

Example 4

6.31 grams of melamine, 5.45 grams of PMDA and 25 grams of MIBK (methyl isobutyl ketone) were mixed in a round bottom flask. The mixture was refluxed under nitrogen for 90 minutes. The mixture was cooled to room temperature. A sample was dried. IR spectra of the dried sample showed the formation of isoimide (peaks at 1836 & 1769 $cm^{-1}$). Reaction was complete to the di-isoimide and no imide was detected.

Example 5

5.81 grams of melamine, 5.00 grams of PMDA, 10 grams of DMF and 10 grams of ethyl acetate were mixed overnight in a flask at room temperature. Reaction was complete to the di-isoimide and no imide was detected. A small sample was dried. IR spectra of the dried sample showed the formation of isoimide (peaks at 1836 & 1769 $cm^{-1}$).

Example 6

5.81 grams of melamine, 5.00 grams of PMDA, 10 grams of MIBK, and 10 grams of toluene were mixed overnight in a flask at room temperature. A small sample was dried. IR spectra of the dried sample showed the formation of isoimide (peaks at 1836 & 1769 $cm^{-1}$). Reaction was complete to the di-isoimide and no imide was detected.

Example 7

3 grams of Vamac® G (from DuPont) and 12 grams of MEK were mixed in a round bottom flask to form a solution. 3.30 grams of a phenol/formaldehyde resin (GP 5300 from Georgia Pacific), and 15 grams of DMF were added to the round bottom flask, and mixed to form a solution. 3.48 grams of melamine and 3.01 grams of PMDA were added to the solution. The solution was heated under nitrogen for 30 minutes at 100° C., 30 minutes at 120° C., and 60 minutes at 140° C. The mixture was cooled to room temperature. A small sample from the mixture was washed thoroughly in MEK (to remove GP5300 and Vamac-G). IR spectra show the formation of isoimide (peaks at 1836 & 1769 $cm^{-1}$) The anhydride and melamine peaks disappeared while the isoimide peaks appeared, and a small amount of imide was also present as indicated by a very small peak at 1734 $cm^{-1}$.

Example 8

2.90 grams of carboxyl-terminated butadiene-acrylonitrile rubber (CTBN rubber, 1300×13 from CVC Thermoset Specialties), 3.78 grams of melamine, 3.27 grams of PMDA and 15 grams of dry MEK were mixed in a round bottom flask. The solution was refluxed under nitrogen for 5 hours. The mixture was cooled to room temperature. A small sample from the mixture was washed thoroughly in MEK (remove CTBN). IR spectra of this sample showed the formation of isoimide (peaks at 1836 & 1769 $cm^{-1}$). The anhydride and melamine peaks disappeared. A small amount of imide was present.

Comparative Example A

In a reaction vessel, 25.22 grams of melamine (0.2 moles), 21.81 grams of PMDA (0.1 moles) and 125 ml DMF were refluxed for 5 hours. The mixture was cooled and quenched with methanol. The solid product was filtered and dried. The IR spectra of the filtered solid product showed the disappearance of the PMDA peaks at 1856 & 1805 $cm^{-1}$ and of the melamine peak at 1558 $cm^{-1}$ and the appearance of the imide peaks at 1788 & 1732 $cm^{-1}$.

Comparative Example B

In a reaction vessel, 50.45 grams of melamine (0.4 moles), 43.62 grams of PMDA (0.2 moles) and 400 ml of NMP (N-methylpyrrolidinone) were refluxed for 30 minutes. The mixture was cooled and quenched with methanol. The solid product was filtered and dried. The IR spectra of the filtered solid product showed imide formation (peaks at 1788 & 1732 $cm^{-1}$).

Example 9

3.50 grams of the di-isoimide dispersed in 9.5 grams of cyclohexanone, prepared in Example 3 supra, and 11.5 grams of a copolymer of butadiene and acrylonitrile modified to contain free carboxylic groups (Nipol 1072J from Zeon Chemicals) dissolved in 63 grams of MEK, were mixed in a flask. 11.20 grams of melamine phosphate/melamine polyphosphate/melamine pyrophosphate flame retardant (Phosmel 200 Fine from Nissan Chemical Industries) was then added and mixed in, to form a first solution/dispersion. 9.10 grams of an epoxy-rubber adduct (HyPox RK84L from CVC Thermoset Specialties) was dissolved in 9.10 grams of MEK to form a second solution. The second solution was added to the first solution/dispersion thereby forming an epoxy solution/dispersion. The epoxy solution/dispersion so prepared was coated onto 12 micrometer thick Kapton® 50FPC polyimide film using a 7 mil gauge (177.8 micrometer) doctor blade followed by removal of the solvent by placing the thus-cast film and substrate in a vacuum oven at 60° C. for one hour, to form an approximately 25 micrometer thick coating.

The thus prepared coated Kapton® was then used as a cover-layer on the PWB test sheet. Referring to FIG. 1, the Kapton® 50FPC film, 1, coated with the curable composition, 2, thus prepared was contacted, 5, to the copper conductive strips, 3, of the PWB test sheet, 4, the curable composition, 2, being in direct contact with the copper conductive strips, 3. The printed wiring board thereby formed, 6, was then consolidated, 7, under vacuum in an OEM Laboratory Vacuum Press by holding the printed wiring board at 175° C. and 2.25 MPa for 80 minutes, thereby forming a flexible printed wiring board, 8, having fully encapsulated copper conductive pathways.

Example 10

3.50 grams of the di-isoimide dispersed in 9.5 grams of cyclohexanone, as prepared in Example 3. and 9.80 grams of "Nipol 1072J" rubber dissolved in 55 grams of MEK were mixed in a flask. The mixture was stirred for 30 minutes. 1.40 grams of CTBN (Carboxyl-Terminated Butadiene-Acrylonitrile Rubber, CTBN 1300×13 from CVC Thermoset Specialties) and 11.20 grams of "Phosmel 200 Fine" flame retardant (from Nissan Chemical Industries) were added to the mixture. 9.10 grams of HyPox RK84L were dissolved in 13.7 grams of MEK and the solution so formed was added to the mixture. The thus prepared solution/dispersion was coated onto a 12 micrometer thick Kapton® 50ENS polyimide film using a 7 mil gauge (177.8 micrometers) doctor blade, after which the thus coated Kapton® film was placed into an air circulating oven at 110° C. for 10 minutes to remove the solvent. The dry adhesive film thickness was 27 micrometers.

The thus prepared coated Kapton® film was used to prepare a fully encapsulated flexible printed wiring board employing the materials and procedures described in Example 9.

Example 11

61.60 grams of "Nipol 1072J" rubber were dissolved in 350 grams of MEK in a flask to form a first solution. 9.10 grams of the di-isoimide dispersed in 25 grams of cyclohexanone prepared in Example 3 was mixed into the first solution to form a second solution/dispersion, followed by mixing in 42.25 grams of "Phosmel 200 Fine" flame retardant (from Nissan Chemical Industries) to form a third solution/dispersion. 34.45 grams of HyPox RK84L was dissolved in 34.45 grams of MEK and the resulting fourth solution was mixed into the third solution/dispersion to form a fifth solution/dispersion. 2.6 grams of bisphenol A diglycidyl ether epoxy resin (EPON™ 828 from Hexion Specialty Chemicals) were mixed into the fifth solution/dispersion to form an epoxy solution/dispersion. The thus prepared epoxy solution/dispersion was coated onto a Kapton® 50FPC polyimide film using a 7 mil gauge (177.8 micrometer) doctor blade. The thus coated Kapton® film was placed in an air circulating oven at 110° C. for 10 minutes to remove the solvent. The dry coating thickness was approximately 25 micrometers in thickness.

The thus prepared coated Kapton® film was used to prepare a fully encapsulated flexible printed wiring board employing the materials and procedures described in Example 9.

Example 12

55.8 grams of a cyclohexanone dispersion of melamine-PMDA di-isoimide (26.9 weight % isoimide content) prepared according to the method of Example 3 and 51.0 grams of rubber (copolymer of butadiene and acrylonitrile modified to contain free carboxylic groups—Nipol 1072J from Zeon Chemicals) were dissolved in 289 grams of MEK to form a solution. 36 grams of an epoxy-rubber adduct (HyPox RK84L from CVC Thermoset Specialties) and 48.0 grams of melamine phosphate/melamine polyphosphate/melamine pyrophosphate flame retardant (Phosmel 200 Fine from Nissan Chemical Industries) were mixed into the solution using a mechanical stirrer. When all the ingredients were dispersed into the solution, the mixture so formed was homogenized for 2.5 minutes (Silverson model L5M homogenizer) to a dispersion having a visually uniform appearance. The thus homogenized mixture was then mechanically stirred continuously until coating, described infra, was commenced.

The dispersion so prepared was coated onto Kapton® 50FPC polyimide film using a 7 mil gauge (177.8 micrometer) doctor blade. The solvent was removed by placing the thus coated Kapton® film in an air circulating oven for 10 minutes at 110° C. The dried coating thickness was approximately 25 micrometers.

The thus dried coated film was laminated to a PWB test sheet. The printed wiring board, 6, as shown in FIG. 1 was further prepared with a release film and a rubber pad on each side. The combination thus prepared was inserted into a quick lamination press and pressed at a temperature of 185° C. and a pressure of 9.8 MPa for 2 minutes, followed by a cure in an air-circulating oven at 160° C. for 90 minutes.

The adhesion of the coated film to the PWB test sheet was determined to be 2.16 N/mm (Newton/millimeter) according to ISO 6133 IPC-TM-650 2.4.9 using a German wheel attached to an Instron machine.

Example 13

The materials and procedures of Example 12 were employed, except that the quantities were different, as indicated in Table 1, and the procedure was modified as described infra.

|  | Ex. 12 (g) | Ex. 13 (g) |
| --- | --- | --- |
| Melamine-PMDA isoimide (26.9 weight-% isoimide) dispersion in Cyclohexanone | 55.8 | 33.85 |
| Nipol 1072J | 51.0 | 41.6 |
| MEK | 289 | 235.7 |
| HyPox RK84L | 36 | 34.5 |
| Phosmel 200 Fine | 48.0 | 42.25 |

The melamine-PMDA isoimide cyclohexanone dispersion, Nipol 1072J, and MEK were combined to form a first solution, to which the Phosmel 200 Fine was added to form a first solution/dispersion. The HyPox RK84L was first dissolved in 34.5 grams of MEK to which 2.6 grams of Epon 828 (from Hexion) were added, thus forming a second solution. The second solution was then added to the first solution/dispersion. The remaining procedures and method of Example 12 were then followed. The adhesion of the coated film on the PWB test sheet was determined to be 2.15 N/mm.

I claim:
1. A di-isoimide compound represented by Structure I

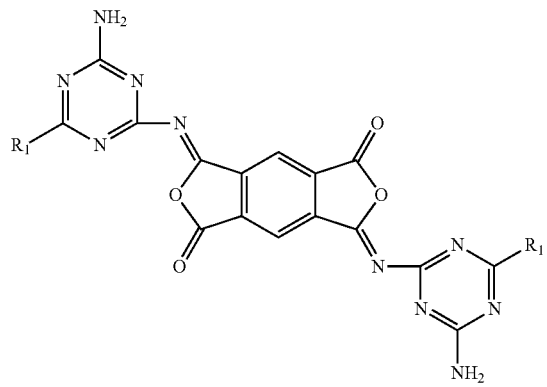

wherein $R_1$ is H, halogen, hydrocarbyl, hydrocarbyloxy, hydrocarbylthio, amido, sulfonamido, cyclic amino, acyl, morpholino, piperidino, or NR'R" where R' and R" are independently H, alkyl or aromatic, substituted or unsubstituted.

2. The compound of claim 1 wherein $R_1$ is $NH_2$.

* * * * *